(12) United States Patent
Colman et al.

(10) Patent No.: US 9,186,473 B2
(45) Date of Patent: *Nov. 17, 2015

(54) ENDOSCOPIC BITE BLOCK

(71) Applicant: ORIDION MEDICAL (1987) LTD., Jersualem (IL)

(72) Inventors: Joshua Lewis Colman, Jerusalem (IL); Gershon Levitsky, Jerusalem (IL); Ron Porat, D.N.Huelu (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/044,870

(22) Filed: Oct. 2, 2013

(65) Prior Publication Data
US 2014/0039339 A1 Feb. 6, 2014

Related U.S. Application Data

(63) Continuation of application No. 10/557,327, filed as application No. PCT/IL2004/000430 on May 20, 2004, now Pat. No. 8,555,886.

(60) Provisional application No. 60/472,368, filed on May 20, 2003.

(51) Int. Cl.
*A61M 16/04* (2006.01)
*A61B 1/00* (2006.01)
(Continued)

(52) U.S. Cl.
CPC ........ *A61M 16/0493* (2014.02); *A61B 1/00154* (2013.01); *A61B 1/24* (2013.01); *A61B 5/097* (2013.01); *A61M 16/0488* (2013.01); *A61M 16/0666* (2013.01); *A61B 1/015* (2013.01); *A61B 2019/204* (2013.01)

(58) Field of Classification Search
CPC ............ A61M 16/0488; A61M 16/04; A61M 16/0463; A61M 16/049; A61M 16/0493; A61M 16/0495; A61M 16/0497; A63B 71/085; A63B 2071/086; A63B 2071/088; A61F 5/56; A61F 5/566; A61F 2005/563; A61C 7/08; A61B 1/24
USPC .......... 128/200.26, 859, 207.18, 207.14, 861, 128/912, 207.17
See application file for complete search history.

(56) References Cited

U.S. PATENT DOCUMENTS 2,669,988 A 2/1954 Carpenter
4,112,936 A 9/1978 Blachly
(Continued)

*Primary Examiner* — Justine Yu
*Assistant Examiner* — Colin W Stuart
(74) *Attorney, Agent, or Firm* — Rodney J. Fuller; Booth Udall Fuller, PLC

(57) ABSTRACT

An endoscopic bite block, with teeth position defining regions which guide the subject's teeth to grip the bite block in their natural position, with the teeth of the upper jaw positioned further out than the lower jaw teeth. These teeth position defining regions are also preferably curved to match the curved shape of the jaw. The upper and lower parts of the front plate of the bite block may also be positioned at different distances out, so that upper and lower lip regions both contact the front plate snuggly. The bite block may be used with separate oral/nasal cannulae, or may incorporate breath sampling or gas supply cannulae. A flexible flapped curtain at the outer end of the bite block may be provided to largely enclose the inner volume of the bite block to enable more accurate capnographic sampling under conditions of wide-open mouth breathing.

12 Claims, 7 Drawing Sheets

(51) Int. Cl.
  *A61M 16/06* (2006.01)
  *A61B 5/097* (2006.01)
  *A61B 1/24* (2006.01)
  *A61B 19/00* (2006.01)
  *A61B 1/015* (2006.01)

(56) References Cited

U.S. PATENT DOCUMENTS

| | | |
|---|---|---|
| 4,640,273 A | 2/1987 | Greene |
| 5,031,611 A | 7/1991 | Moles |
| 5,046,491 A | 9/1991 | Derrick |
| 5,174,284 A | 12/1992 | Jackson |
| 5,273,032 A | 12/1993 | Borody |
| 5,355,874 A | 10/1994 | Bertram |
| 5,413,095 A | 5/1995 | Weaver |
| 5,431,158 A | 7/1995 | Tirotta |
| 5,513,634 A | 5/1996 | Jackson |
| 5,590,643 A | 1/1997 | Flam |
| 5,623,924 A | 4/1997 | Lindenman |
| 5,638,811 A | 6/1997 | David |
| 5,803,079 A | 9/1998 | Rogers |
| 5,950,624 A * | 9/1999 | Hart ............... 128/207.15 |
| 6,257,238 B1 | 7/2001 | Meah |
| 6,422,240 B1 | 7/2002 | Levitsky |
| 6,517,549 B1 * | 2/2003 | Dennis ............... 606/108 |
| 6,758,212 B2 | 7/2004 | Swann |
| 6,792,943 B2 | 9/2004 | Kumar |
| 6,851,424 B2 | 2/2005 | Scopton |
| 6,916,287 B2 | 7/2005 | Dematteis |
| 8,555,886 B2 | 10/2013 | Colman |
| 2002/0092526 A1 | 7/2002 | Bertoch |
| 2002/0151871 A1 | 10/2002 | Gaiser |
| 2003/0024533 A1 | 2/2003 | Sniadach |
| 2003/0234016 A1 | 12/2003 | Swann |
| 2004/0025887 A1 | 2/2004 | Scopton |
| 2010/0198096 A1 | 8/2010 | Colman |

* cited by examiner

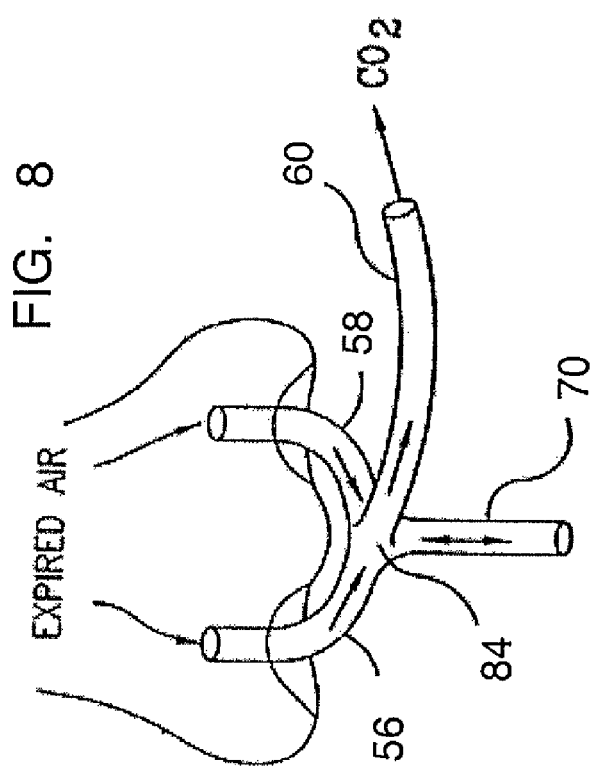

ENDOSCOPIC BITE BLOCK

CROSS-REFERENCE TO RELATED APPLICATIONS

This application is a continuation of U.S. patent application Ser. No. 10/557,327, filed Nov. 21, 2005, which is the U.S. National Stage of International Application No. PCT/IL2004/000430, filed May 20, 2004, which claims the benefit of U.S. Provisional Application No. 60/472,368, filed May 20, 2003, the contents of each of which are expressly incorporated herein in their entireties.

FIELD OF THE INVENTION

The present invention relates to the field of bite blocks for endoscopic use, adapted to provide for optimum subject comfort and tolerance, and especially such endoscopic bite blocks with incorporated gas sampling or delivery cannulae or for use with separate cannulae.

BACKGROUND OF THE INVENTION

A bite block is a device commonly used during upper gastro-intestinal endoscopic procedures to facilitate passage of an esophago-gastro-duodenoscopy (EGD) endoscope. The purpose of the bite block is to allow the physician to perform the procedure without the subject interfering by biting and damaging the endoscope tubing inserted via his mouth, whether voluntarily or involuntarily.

The upper gastro-intestinal endoscopic procedure itself, together with the use of a bite block, is often highly uncomfortable for the subject. For this reason it is very common for the subject to be sedated during the procedure. The sedative helps the subject to tolerate the procedure, rather than to oppose it, thus enabling the doctor to perform the procedure undisturbed.

Despite this, it is common for the subject to show opposition to the procedure. The subject will often resist entry of the endoscope by not swallowing as requested and by tensing his or her muscles. The subject will also often oppose the placement of the bite block itself before the procedure, and more commonly during the procedure because of involuntary muscular reactions, by trying to manipulate it out of his or her mouth by means of the tongue or teeth.

Prior art bite blocks are generally characterized by a number of structural features:
1. A tubular body or barrel whose internal lumen serves as the channel for passage of the endoscope, and whose top and bottom outer surfaces serve as the surfaces upon which the subject's teeth bite. These surfaces are generally flattened.
2. A wall centrally connected to the outer end of the tubular body, shaped such that it should lie comfortably outside and around the subject's mouth. It is this wall that fulfils the double function of providing a general alignment direction to the tubular body and of preventing the bite block from falling into the mouth. The wall is also known as the front plate.
3. A band connected to the bite block and used to strap the bite block firmly to the subject.

A number of bite blocks are described in the prior art, which add additional features to the above-mentioned basic features. The additional features are generally directed to assisting the physician in performing the endoscopic procedure with minimum interference from the subject, by making it more difficult for the subject to oppose the bite block, which generally means making it more difficult for the subject to eject the bite block from the mouth. Thus in U.S. Pat. No. 5,174,284 to F. W. Jackson for "Endoscopic bite block", there is described a bite block with, inter alia, (i) a tubular outer surface whose upper and lower walls are sloped towards each other in the direction of the front plate, so that as the subject's teeth bite down on the surfaces, the bite block tends to move back into the mouth where it seats more firmly; and (ii) a tongue depressor, which firmly forces the tongue downwards as the teeth compress against the upper and lower surfaces of the bite block channel, keeping the tongue seated below the mouthguard, where it cannot struggle to push the block out of the mouth. Additionally, the bite block has rear teeth guards, which require the mouth to open very wide in order for the bite block to fall out. In U.S. Pat. No. 6,257,238 to N. M. Meah, for "Bite block for upper gastrointestinal endoscopy with tongue depressor", there is described another bite block with a tongue depressor, though the tongue depressor is therein described as preventing the tongue from covering the channel of the bite block, and blocking the subject's throat.

One of the physiological, effects of the use of such bite blocks is that a sensation of oral immobility may be generated because of the way in which such bite blocks operate. The bite block may thus be uncomfortable for the subject and may produce a feeling of being gagged even before the insertion of the endoscope itself. Furthermore, large amounts of saliva are commonly produced during these procedures, and since one method of dealing with saliva is by manipulating it with the tongue, depressing the movement of the tongue may prevent the subject from dealing with it, again causing the subject to have a choking feeling. This general physiological feeling may increase the subject opposition to the procedure even more, thus negating the initial, intended purpose of the invention.

In addition to the problems associated with the comfort and ease of use of prior art endoscopic bite blocks, a further problem exists when such prior art bite blocks are used together with breath sampling means, in particular capnographic sampling, or gas delivery, such as oxygen. It is common in endoscopic procedures for the doctor to try to reduce the opposition of the subject to the procedure by administering sedatives. However, as with all sedation procedures, careful monitoring of the subject must then be performed, usually on a continuous or semi-continuous basis, to avoid the adverse affects of over-sedation.

It is well known that a sedated subject is vulnerable to episodes of hypo-ventilation and apnea. The ability to adequately monitor and detect these episodes is essential when potent sedatives are employed. Pulse oximetry, to determine the blood $SpO_2$ level, is routinely used during these procedures, and provides a sensitive and reliable estimate of arterial blood oxygenation. While breathing room air, apnea causes arterial oxygen de-saturation and can thus be speedily detected by means of pulse oximetry. However, when subjects receive supplemental oxygen, as is recommended during sedation where breathing may be suppressed, apnea-induced oxygen de-saturation would be delayed until hypercapnia ensued. For this reason, capnography, the continuous measurement of carbon dioxide in the breath, is generally recommended as a more appropriate and direct means to monitor for hypo-ventilation and apnea.

During medical procedures other than upper gastro-intestinal endoscopy the sedated subject is easily monitored with a capnograph, which continuously samples the subjects' breath. This is realized using an appropriate breath sampling cannula device connecting between the subject and the capnograph. The cannula is appropriately positioned in close proximity to the subject's nose, or nose and mouth. The capnograph, using a pump, continuously extracts breath from the subject via the cannula, to the capnograph sensor for analysis. One example of such a sampling cannula device is described in U.S. Pat. No. 6,422,240 to G. Levitsky et al, for "Oral/Nasal Cannula", assigned to the assignee of the present application, and herewith incorporated by reference in its entirety.

In the prior art, $CO_2$ sampling during upper gastro-intestinal endoscopy, and especially during long duration procedures performed under sedation, monitoring is often performed using a separate nasal or oral/nasal cannula in conjunction with the bite block. Concomitant use of prior art bite blocks and cannulae is often not an optimal solution, and the capnographic performance may be noticeably affected. The generally applied method of using a prior art adjunct oral/nasal cannula with a prior art bite block, is to put on the oral/nasal cannula after the bite block has been inserted, such that the oral prong sits outside of the front plate of the bite block and is often mis-positioned or occluded by the bite block, or is located directly in the path of the endoscope and consequently pushed aside or even bent back when the endoscope is inserted. There is essentially "competition" for the use of the subject's oral passage between the need for oral breath sampling and the need for the passage of the endoscope, and since the endoscope procedure is the mission being undertaken, it generally prevails over the needs of the capnographic sampling.

The alternative use of a nasal sampling cannula, in an attempt to overcome this problem, is generally inadequate, since it is known that during upper gastrointestinal endoscopic procedures, it is usual for the subject to perform largely oral breathing alone, and the effectiveness of the nasal sampling is much reduced. However, if oral/nasal sampling is performed in an attempt to overcome this problem, even if the oral sampling opening is placed in such a position so as not to interfere with the region required for the insertion and maneuvering of the Endoscope, the existence of majority oral exhalation still leads to another problem when using prior art devices. When the subject's mouth is wide open, as it is during upper G-I endoscopy, the excess breath pressure within the oral cavity is very small, and the exhaled breath therefore becomes diluted with the inhaled air, and sampling is thus inaccurate.

For the delivery of supplementary oxygen during endoscopic procedures, there exist in the prior art, a number of combination bite block/oxygen delivery cannula devices, such as those described in U.S. Pat. No. 5,273,032 to T. J. Borody, for "Oxygenating oral medical appliance" and in U.S. Pat. No. 5,513,634, to F. W. Jackson, for "Combination integral bite block airway and nasal cannula", both herewith incorporated by reference, each in its entirety.

Both of these patents describe methods for delivering supplemental oxygen during upper gastro-intestinal endoscopy from a single, integrated device. Unlike the situation with carbon dioxide sampling, the use of a single device that integrates the bite block with oxygen delivery is mainly important for convenience, and is not mandated for providing optimal performance. A standard, separate oxygen supply nasal cannula could readily be positioned so as to adequately provide oxygen to the subject even when a separate bite block is in place. This is not the case when a separate breath sampling cannula is used simultaneously with a separate prior art bite block, as explained above.

One possible disadvantage of the integrated device described in U.S. Pat. No. 5,273,032 is that the oxygen is delivered via two tunnels with ends that do not reach the nasal cavities, but instead direct the oxygen gas stream towards the nasal cavities. The ability of these devices to efficiently direct the oxygen gas stream to the nasal cavities is thus dependant on how well the bite block sits in its intended position within the subject's mouth. Any tilt of the bite block inevitably causes a tilt in the direction of the nasal tunnels and consequently misdirects the oxygen gas stream away from the subject's nostrils. Such tilting of prior art bite blocks, or of the combination bite block/cannula device of U.S. Pat. No. 5,273,032 is common, as described hereinabove, either because of a feeling of discomfort when the bite block is in the mouth, causing the subject to attempt to move it, or because of the tilt generated by the placement position of the teeth in such prior art bite blocks, as explained above. The integrated device described in U.S. Pat. No. 5,513,634, on the other hand, is equipped with nasal prongs of a soft material, that do reach the nostrils of the subject. However, even with this device, tilting of the bite block causes the prongs to be tilted also, and may consequently cause them to exit the nostrils. The correct seating of the bite block is therefore likely to have an effect also on the efficacy of oxygen delivery also.

There therefore exists a need for an endoscopic bite block which fits comfortably into the mouth of the subject, without imposing any unnatural constraints on the subject's oral position, and consequently which reduces sensations in the subject that would cause the subject to oppose its presence. Furthermore, there exists a need for such an endoscopic bite block which enables accurate breath sampling, even in conditions of open mouth oral breathing, and which does not interfere with the endoscopic procedure.

The disclosures of each of the publications mentioned in this section and in other sections of the specification, are hereby incorporated by reference, each in its entirety.

SUMMARY OF THE INVENTION

The present invention seeks to provide a new endoscopic bite block, which overcomes some of the disadvantages of prior art bite blocks, related to a possible lack of comfort of such bite blocks when seated in the subject's mouth, to the ability to deliver supplementary oxygen reliably and to sample the patient's breath effectively, and to the problems of efficient wide-open mouth oral breath sampling. According to a first preferred embodiment of the present invention, the bite block differs from prior art bite blocks in that means are provided on the outer upper and lower surfaces of the tubular body for ensuring that the subject's teeth grip the bite block in the teeth's natural position, without the need for the subject to force his or her lower jaw into an uncomfortable position. Since the upper jaw tooth line is generally disposed further out in the mouth than the lower jaw teeth, this is preferably accomplished in the bite block of the present invention, by providing means to ensure location of the top teeth further forward on the tubular body than the bottom teeth, such as by provision of suitably located grooves or stepped regions in the outer surfaces to locate both sets of teeth appropriately. These grooves or stepped regions are also preferably curved to match the curved shape of the human jaw. Consequently, even though the upper teeth are located further forward than, the lower teeth, it is found that because of the natural gripping position of the teeth, use of the bite block of the present invention does not result in the generation of moments which attempt to tilt the bite block out of its optimal location. This is in contrast to prior art bite blocks with teeth gripping positions aligned opposite each other, where, because of the forced unnatural position of the lower jaw, the bite block may tend to tilt under the action of spontaneous movements of the lower jaw to relieve the discomfort.

Furthermore, according to another preferred embodiment of the present invention, the front plate at the outer end of the bite block, which should lodge firmly against the lips of the subject, is preferably shaped such that it is not set at a uniform distance at the outer end of the tubular body, but rather, the top region is set further out than the bottom section, such that the natural position of the subject's upper lip region, projecting further out from his or her face than the lower lip region, does not prevent the front plate of the bite block from sitting firmly against both sets of lips. Such positioning of the front plate firmly against the whole of the subject's mouth also assists in overcoming any tendency for the bite block to tilt out of the subject's mouth because of moments generated should the subject move his teeth from the optimal natural gripping position.

Additionally, according to yet another preferred embodiment of the present invention, the attaching points of the band for strapping the bite block round the back of the subject's head may be generally set above the horizontal center line of the front plate, such that a moment is generated which tends to exert a stronger pull on the top section of the front plate than on the bottom section, such that the whole bite block undergoes a moment which acts to counteract any undesired moment generated by the teeth of the subject.

The bite blocks of the present invention can also preferably be provided either with built-in sampling and gas delivery passages, such that the bite block has an integrated capnographic cannula and oxygen delivery system, or as a bite block for use with a separate oral/nasal cannula. According to a further preferred embodiment of the present invention, an endoscopic bite block intended for use with a separate oral/nasal cannula is described, in which the oral sampling is performed by means of an opening in the roof of the bite block central channel, with the end of the oral sampling prong of the cannula sitting on the inner surface of the front plate, closed between the plate and the patient's upper lip. The oral prong may preferably be inserted into this opening such that its tip just projects into the top of the channel, though this is not essential. The oral prong of the cannula is thus able to operate without being disturbed by, and without disturbing, the insertion of the endoscopic probe through the bite block. A groove is also preferably provided in the top of the front plate to firmly locate the oral prong in its correct position between the subject's upper lip and the front plate.

Furthermore, according to yet another preferred embodiment of the present invention, the cross sectional area of the bite block inner channel is substantially closed off near its outer end by means of a flexible curtain, which maintains a generally closed inner volume for the central channel of the bite block. The flexible curtain has flaps such that it opens partially when the endoscope is inserted, and even enables the physician to maneuver the endoscope around while feeding it into the patient's esophagus, but still maintains a largely closed oral cavity volume. A small hole is preferably provided in this flexible curtain so that the subject's oral breathing can continue, largely through this hole. The closed oral cavity volume prevents excess mixing of the exhaled breath stream with air from outside the mouth, such that capnographic sampling can be accurately performed on undiluted breath as it is exhaled. Furthermore, the hole in the flexible curtain is preferably located close to the sampling opening in the roof of the bite block, such that the capnographic measurement is performed on an accurately representative sample of the exhaled and inhaled breath stream. In the capnographic bite block according to this preferred embodiment, the operation of the small hole and the sampling opening disposed close to it can be readily understood by considering these elements to be comparable to the effect of normal oral breath sampling without the use of a bite block. In this situation, the breath passing in and out of the large oral cavity, is sampled by the oral prong as it passes in a stream through the small opening of the subject's lips—at least in comparison to the cross sectional area of the mouth. Likewise with the capnographic bite block of the present invention, the breath passing in and out of the large combined internal volume of the oral cavity and the bite block is sampled by the sampling opening as it passes in a stream through the small hole in the flexible curtain. The bite block thus enables more efficient and accurate capnographic sampling than with prior art bite blocks under conditions of wide-open mouth breathing, which is common in endoscopic procedures.

Additional advantages of bite blocks according to the various preferred embodiments of the present invention, arise as a result of their correct and stable positioning within the mouth of the subject. When the bite block has an incorporated breath sampling cannula or a gas delivery system, or both, then the stability of the positioning of the bite block of the present invention in the user's mouth ensures that the desired breath sampling point or points, or the desired gas delivery point or points, are maintained during the procedure, and the tendency for the subject to push out or move the bite block, which would misplace the sampling or delivery ports, is significantly reduced in comparison with prior art bite blocks. Additionally, when a separate oral/nasal cannula is used the firm placement of the subject's lips against the front plate of the bite block of the present invention assists in keeping the oral prong in its correct location sandwiched between the front plate and the subject's upper lip.

There is therefore provided, in accordance with a preferred embodiment of the present invention, an endoscopic bite block, comprising:

(i) a tubular body comprising an inner end section adapted for insertion into the mouth of a subject, an outer end section adapted for insertion of an endoscopic probe, a central channel, an upper wall having an upper outer surface, and a lower wall having a lower outer surface, (ii) a front plate connected to the outer end section of the tubular body, (iii) teeth positioning regions across at least part of the upper and lower outer surfaces, the teeth positioning region in the upper surface being disposed outwardly relative to the teeth positioning region in the lower surface. At least one of the upper and lower surfaces preferably has a generally flattened portion on which its associated teeth positioning region is disposed. Additionally, at least one of the teeth positioning regions is preferably curved in the plane of its associated surface to approximate the curve of the teeth in a human jaw. In accordance with more preferred embodiments of the present invention, in the above described bite block, at least one of the teeth positioning regions may be a groove in its associated surface, or a lowered platform region in its associated surface.

Additionally and preferably, the front plate of the bite block has its upper section disposed outwardly relative to its lower section. The bite block also preferably comprise connecting points for attaching the bite block to the subject, and the connecting points are preferably located above the horizontal center line of the bite block.

There is further provided in accordance with still another preferred embodiment of the present invention, a bite block as described above, and also comprising at least one of a gas collecting cannula and a gas delivery cannula, or at least one nasal prong for delivery of gas to the subject. The gas collecting cannula preferably comprises at least one of nasal prongs and an oral collection channel, and in this case, the oral collection channel is preferably disposed in the upper wall such that it enters the central channel in a direction facing the stream of exhaled oral breath. In the above described bite block, the gas delivery cannula preferably comprises at least one of nasal and oral outlets.

In accordance with yet a further preferred embodiment of the present invention, there is also provided an endoscopic bite block, comprising:
(i) a tubular body comprising an inner end section adapted for insertion into the mouth of a subject, an outer end section adapted for insertion of an endoscopic probe, and a central channel, the tubular body having at least one sampling opening in fluid contact with the central channel,
(ii) a front plate connected to the outer end section of the tubular body, and
(iii) a penetrable curtain disposed in the outer end section across the majority of the internal cross section of the tubular body and substantially preventing flow of gases across the majority of the cross section of the tubular body. The penetrable curtain is preferably such that an open area is provided for passage of the orally inhaled and exhaled breath of the subject. The open area is preferably disposed close to the at least one sampling opening, such that the at least one sampling opening samples substantially only the inhaled and exhaled breath of the subject flowing within the tubular body. Preferably, the open area is either a hole in the penetrable curtain, or a gap at an extremity of the curtain. In accordance with yet a further preferred embodiment of the present invention, the penetrable curtain comprises flaps of material peripherally secured to the tubular body.

There is even further provided in accordance with another preferred embodiment of the present invention, an endoscopic bite block as described above, with a penetrable curtain, and wherein the curtain is penetrable by the endoscopic probe such that the majority of the cross section of the tubular body remains substantially closed of to the passage of gases even when the endoscopic probe is maneuvered within the bite block.

In any of the above described bite blocks with a curtain, the curtain is prefer-ably constructed of a transparent material such that visibility into the oral cavity of the subject is maintained.

Furthermore, in accordance with yet another preferred embodiment of the present invention, there is provided an endoscopic bite block as described above with a penetrable curtain, and wherein the sampling opening is connected to an internal sampling passage built into the bite block, such that exhaled breath in the central channel can pass into the internal sampling channel.

There is also provided in accordance with a further preferred embodiment of the present invention, an endoscopic bite block as described above with a penetrable curtain, and also comprising a recessed groove in the upper section of the front plate, and terminating close to the sampling opening, the recessed groove being adapted to receive the oral prong of an oral/nasal cannula. In such embodiments, samples of the inhaled and exhaled breath from the tubular body pass into the oral prong when the prong is inserted into the recessed groove. Furthermore, the oral prong is preferably firmly held in the grooved recess between the front plate and the upper lip of the subject when the endoscopic bite block is inserted into the mouth of the subject. Any of the above described endoscopic bite blocks having a curtain, may also preferably comprise a tubular passage leading upwards from the sampling opening, the tubular passage being adapted to receive the oral prong of an oral/nasal cannula. In such a case, samples of the inhaled and exhaled breath from the tubular body pass into the oral prong when the prong is inserted into the tubular passage.

In accordance with yet more preferred embodiments of the present invention, there is provided an endoscopic bite block with a penetrable curtain as described above, wherein the tubular body also comprises an upper wall having an upper outer surface, and a lower wall having a lower outer surface, the endoscopic bite block also comprising teeth positioning regions across at least part of the upper and the lower outer surfaces, the teeth positioning region in the upper surface being disposed outwardly relative to the teeth positioning region in the lower surface.

At least one of the upper and lower surfaces preferably has a generally flattened portion on which its associated teeth positioning region is disposed. Additionally, at least one of the teeth positioning regions is preferably curved in the plane of its associated surface to approximate the curve of the teeth in a human jaw. In accordance with more preferred embodiments of the present invention, in the above described bite block, at least one of the teeth positioning regions may be a groove in its associated surface, or a lowered platform region in its associated surface. Additionally and preferably, the front plate of the bite block has its upper section disposed outwardly relative to its lower section.

BRIEF DESCRIPTION OF THE DRAWINGS

The present invention will be understood and appreciated more fully from the following detailed description, taken in conjunction with the drawings in which:

FIG. 8 is an illustrative oral/nasal cannula for the collection of exhaled gases with which use of the bite block of FIG. 5 is intended.

DETAILED DESCRIPTION OF PREFERRED EMBODIMENTS

Figure 1:
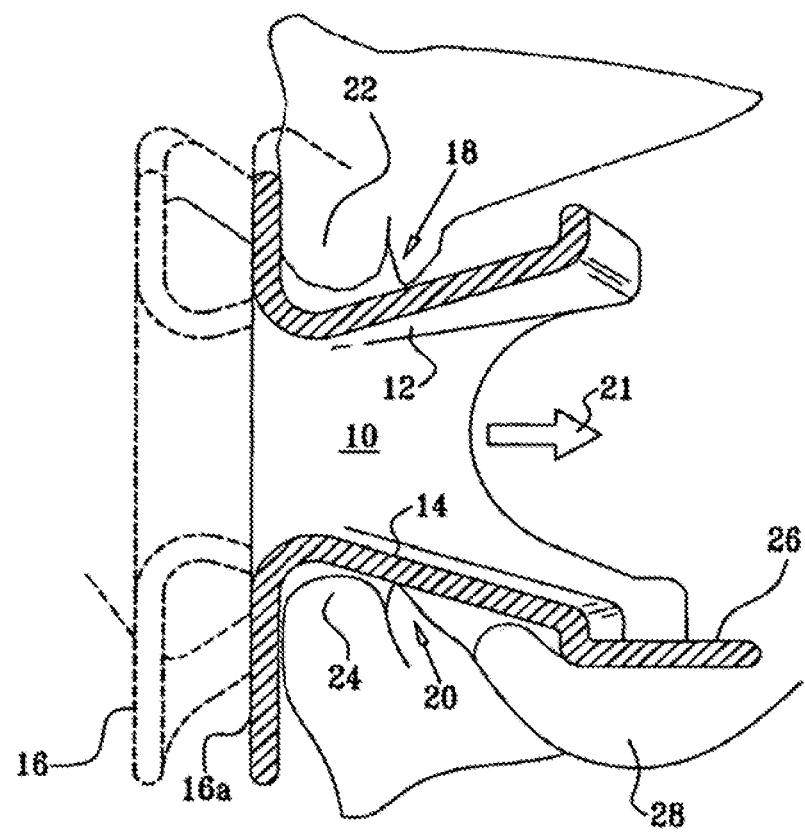
FIG. 1 is a schematic illustration of a prior art endoscopic bite block.

Reference is now made to FIG. 1, which illustrates schematically a prior art endoscopic bite block, such as that described in the above-mentioned U.S. Pat. No. 5,174,284.

The bite block has an internal channel 10, with upper surface 12 and lower surface 14 inclined towards the front of the bite block, where the front plate 16 is connected. As the subject's teeth 18, 20, close, the bite block is pulled into the mouth in the direction 21 by the action of the teeth on the inclined upper 12 and lower 14 surfaces, so that the font plate moves from its initial position 16, until it is lodged firmly up against the subject's lips 22, 24, in position 16a. At the same time, the tongue depressor 26 firmly grips the subject's tongue 28, preventing it from moving.

However, the structure of the human mouth is such that the teeth positions are unlike those shown in the prior art drawing of FIG. 1, in that the upper and lower teeth do not close naturally onto each other, as shown in FIG. 1. The upper jaw and teeth protrude further out from the skull than the lower jaw and teeth. When the human mouth is closed, the jaw morphology naturally causes the upper row of teeth to sit on the lower row at a position forward of the line of the teeth of the lower row. This natural rest position is further facilitated since the curve of the upper jaw teeth has a slightly larger radius than that of the lower jaw teeth. Gripping the bite block of FIG. 1 with the teeth aligned opposite each other, as shown in FIG. 1, is only made possible by pushing the lower jaw forward from its natural rest position. When such a position is held for more than a short time, muscular tension and fatigue readily set in, causing unnecessary discomfort to the subject, in a situation where muscular relaxation is of great importance. This discomfort itself then also generates the urge to move or eject the bite block, using the teeth or tongue. Furthermore, the unnatural position of the lower jaw tends to cause mouth movements, which are operative to tilt the bite block from, its desired position. Such a tilted position, not having a well-defined seated location within the mouth, also generates a lack of support and comfort to the subject, in a situation where both are important to ensure optimum subject tolerance of the bite block and the endoscopic procedure. On the other hand, if the subject grips the bite block with his teeth in their natural rest position, with the upper teeth forward of the lower teeth, then this naturally restful position of the jaw assists in avoiding the generation of moments which may tend to rotate the bite block from its optimum position.

Figure 2A:
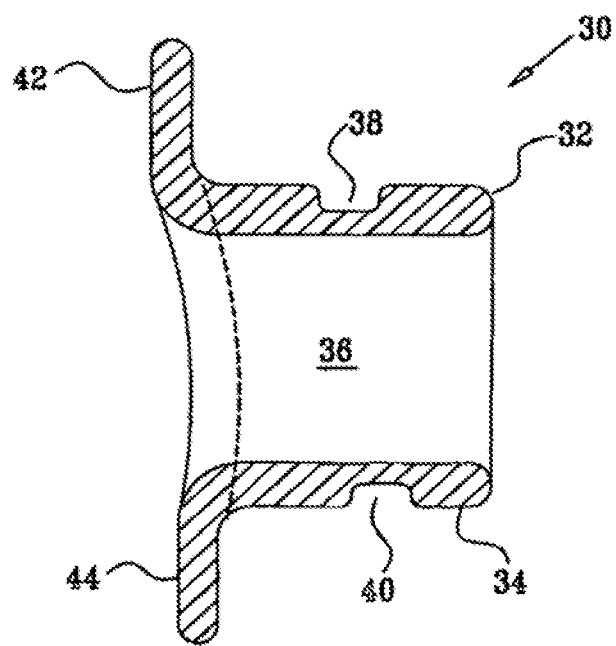
FIGS. 2A to 2C are cut-away, cross-sectional, schematic views of endoscopic bite blocks, constructed and operative according to preferred embodiments of the present invention.

Reference is now made to FIG. 2A, which is a cut-away, cross-sectional schematic view of an endoscopic bite block 30, constructed and operative according to a first preferred embodiment of the present invention. The outer upper and lower surfaces 32, 34, of the bite block channel 36 preferably have grooves positioned according to the approximate position of the teeth in the upper jaw and the lower jaw. The top groove 38 for the top teeth is set slightly forward of the lower groove 40 for the teeth of the lower jaw. The grooves are also preferably curved to approximate the shape of the curve of the tooth line, being of larger curvature for the upper row than for the lower row. The regions where the subject's teeth can hold the bite block are therefore uniquely defined such that the subject keeps the teeth of his upper jaw forward of those of the lower jaw. The barrel of the bite block is thus held firmly between the teeth with a more natural feeling to the subject, and without the subject's jaws being constrained into a non-restful position.

Additionally and preferably, the front plate 42 at the top of the bite block barrel is disposed further forward than the front plate 44 at the bottom of the barrel, to permit both the top lip regions of the subject and his/her bottom lip regions to fit appropriately against both parts of the front plate. This assists in inducing the subject to grip the bite block naturally, also causing it to lie firmly, upright and comfortably in the mouth.

Figure 2B:
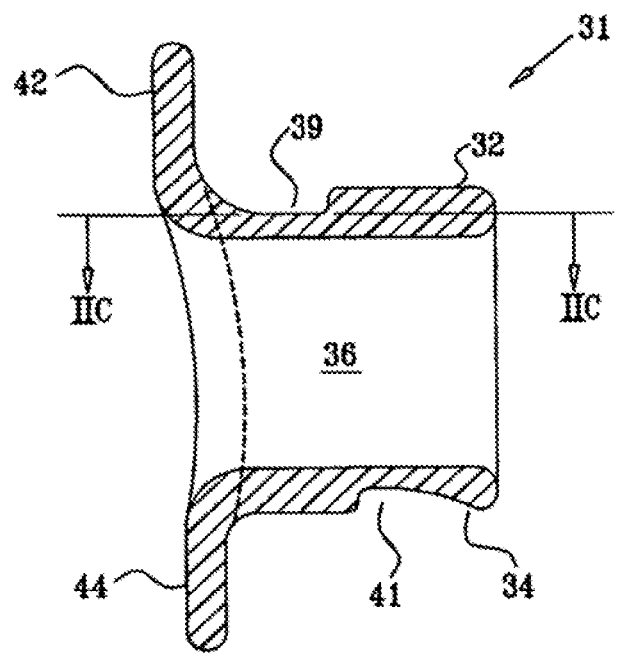

Reference is now made to FIG. 2B, which illustrates a cut-away, cross-sectional schematic view of an endoscopic bite block 31, constructed and operative according to another preferred embodiment of the present invention. The bite block is similar to that shown in FIG. 2A, except that instead of having grooves for the teeth in the top and bottom surfaces of the barrel, a lowered platform region 39 is provided in the top surface. This has the effect of constraining the subject's teeth less rigorously than the grooved embodiment of FIG. 2A, therefore providing a more comfortable gripping position, and especially for different subjects with slightly different shaped teeth curves and positions. Additionally and preferably, on the bottom surface 34, there is provided a sloping stepped depression 41, set further back than the edge of the lowered platform region of the upper surface, which also enables more flexibility in teeth positioning for the lower jaw teeth also.

Figure 2C:
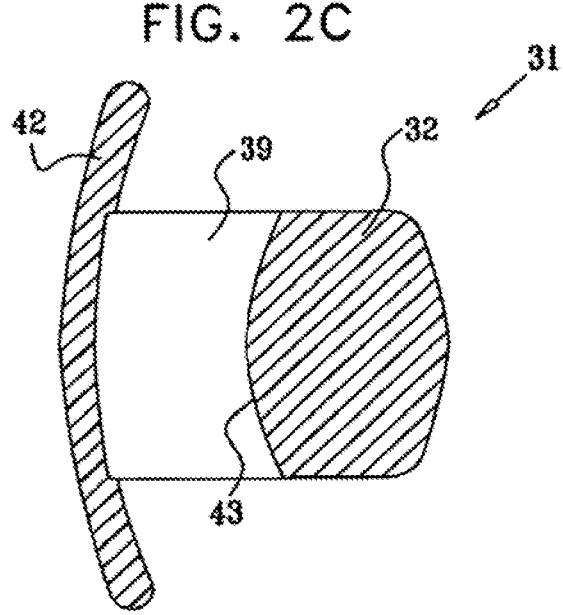

Reference is now made to FIG. 2C, which is a view from above, along section IIC-IIC of FIG. 2B, showing how the edge 43 of the lowered platform region 39 is curved to shape the approximate curve of the subject's upper teeth.

In any of the preferred embodiments shown in FIGS. 2A to 2C, the grooves or lowered regions may preferably be fined with a material softer than that of the body of the bite block, such that the grip of the bite block is made to be more comfortable. Alternatively and preferably, the defining regions for the teeth may be at the same height as the rest of the surface in which they are incorporated, but may be made of softer or harder material to define the teeth gripping positions. Alternatively, even the raised section 32 of FIGS. 2B and 2C may be made of softer material to provide for increased user comfort.

The essence of all of these embodiments of the present invention, whether similar to those shown in FIG. 2A to 2C or not, is that the teeth be directed, by means of a distinctive defining region of the surface, to grip the bite block with the subject's jaws in a natural position and hence in a more relaxed manner. According to different preferred embodiments, this defining region may be of different height, texture, material, or combinations thereof, so long as it adequately fulfils its function of directing the teeth to bite the block with a natural and as relaxed as possible, jaw position.

Figure 3:
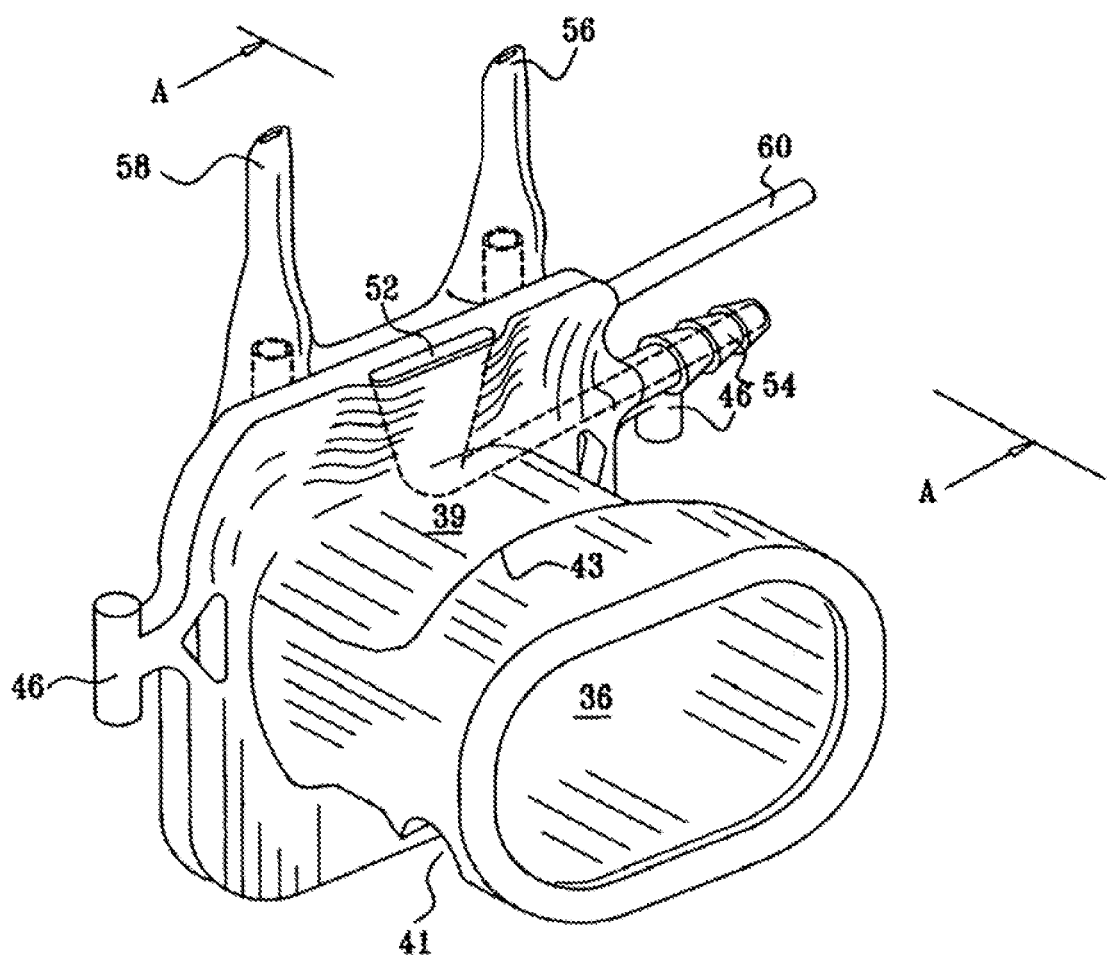
FIG. 3 is an isometric schematic drawing of a bite block, according to another preferred embodiment of the present invention, with integral oral-nasal cannula for oxygen delivery and for oral/nasal breath sampling, and also illustrating the various structural parts of the bite block, shown in the cut-away sectional view of FIG. 2B.

Reference is now made to FIG. 3, which is an isometric schematic drawing of a bite block, according to another preferred embodiment of the present invention, taken from the rear, to illustrate the various structural parts of the bite block shown in the cut-away sectional view of FIGS. 2B and 2C. The various features of FIG. 3 are denoted by the same reference characters as those of FIGS. 2B and 2C. The bite block shown in FIG. 3 differs from those in FIGS. 2A to 2C in that it also incorporates cannulae, both for sampling the subject's breath, and for supplying gas to the subject, as will be discussed hereinbelow. However, the structural features relating to the location or the bite block in the subject's mouth are essentially those of FIGS. 2B and 2C, and these features are now explained.

In the three-dimensional representation shown in FIG. 3, in the upper surface 32 of the tubular body, there is shown a curved lowered platform for the upper teeth 39, whose rear edge 43 is designed to approximately match the curvature of the upper teeth of a human jaw. In the lower outer surface of the tubular body, there is seen a sloping stepped depression 41, set further back than the edge 43 of the lowered platform region of the upper surface, as described hereinabove.

FIG. 3 also illustrates how the bite block of the present invention is preferably attached to the subject's head. Bite blocks generally have lugs or attachment points at the outer edges of the front plate for connecting a band to the front plate to hold the bite block firmly in position against the subject's lips. In prior art bite blocks, these lugs or attachment points are generally located at the center of the height of the front plate, in line with the center line of the bore of the barrel. In FIG. 3, the lugs or attachment points 46, according to this preferred embodiment of the present invention, are located above the center of the height of the front plate, such that the pull of the attaching band tends to exert a stronger pull to the top of the front plate than to the bottom of the front plate, thus assisting to overcome any moment generated by the teeth tending to tilt the bite block outwards, and keeping the bite block seated firmly and upright in the subject's mouth. However, since there may also be a tendency for the subject, to push the bite block out from the bottom with his tongue, which would be assisted by a high attachment, the position of the attachment has to be determined by experience with the actual design of the bite block.

In addition to increasing the comfort and tolerance of the subject to the very presence of the bite block in his mouth during an endoscopic procedure, when a nasal or an oral-nasal cannula for sampling breath or for delivering gas is incorporated into the bite block of the present invention, it is possible to reduce some of the problems of prior art bite blocks with incorporated gas delivery cannulae, or as used with separate sampling cannuale.

Reference is now made again to FIG. 3, to those aspects of the bite block of the present invention relating to the integration of an oral, or a nasal or an oral-nasal cannula for breath sampling, and of an integral gas delivery system, which can be used to supply supplemental oxygen to the subject, generally through a nasal delivery outlet or outlets. The preferred embodiment of the integral bite block/cannula combination shown in FIG. 3 shows an oxygen delivery outlet 52, fed by means of an oxygen supply nipple 54. The delivery outlet 52 should be maintained below the subject's nostrils to provide an effective supply of supplemental oxygen. An internal channel, unseen in FIG. 3, and connected to the delivery nipple, can also supply oxygen to the subject's mouth through the channel of the bite block, if such an option is used. In addition, the bite block of FIG. 3 also shows a pair of nasal prongs 56, 58, preferably operative for the collection of exhaled breath for capnographic monitoring of the subject during the procedure. The exhaled breath is preferably passed to a capnographic monitor through the breath collection tube 60. A sampling channel, unseen in FIG. 3 and connected to the collection tube 60, can also be used to sample the orally exhaled breath of the subject from the channel 36 of the bite block. As it is usual for endoscopic procedures to be carried out with the subject lying on the left side, the oxygen delivery nipple 54 and the breath collection tube 60 are preferably located on the right hand side of the bite block.

The novel structural features of the bite block of the above-described preferred embodiments of the present invention, namely the offset teeth positioning regions, the staggered front plate and the attachment lugs positioned above the bite block center line, encourage the maintenance of the bite block in a predetermined, upright, position within the mouth of the subject, and thus enhance the correct positioning of the breath sampling prongs and/or of the gas delivery outlets, relative to the subject's nostrils and/or mouth, whichever are appropriate. The bite block, according to these additional preferred embodiments of the present invention, thus also provides for correct positioning in the mouth, both for efficient oxygen delivery and for accurate breath sampling.

Figure 4:
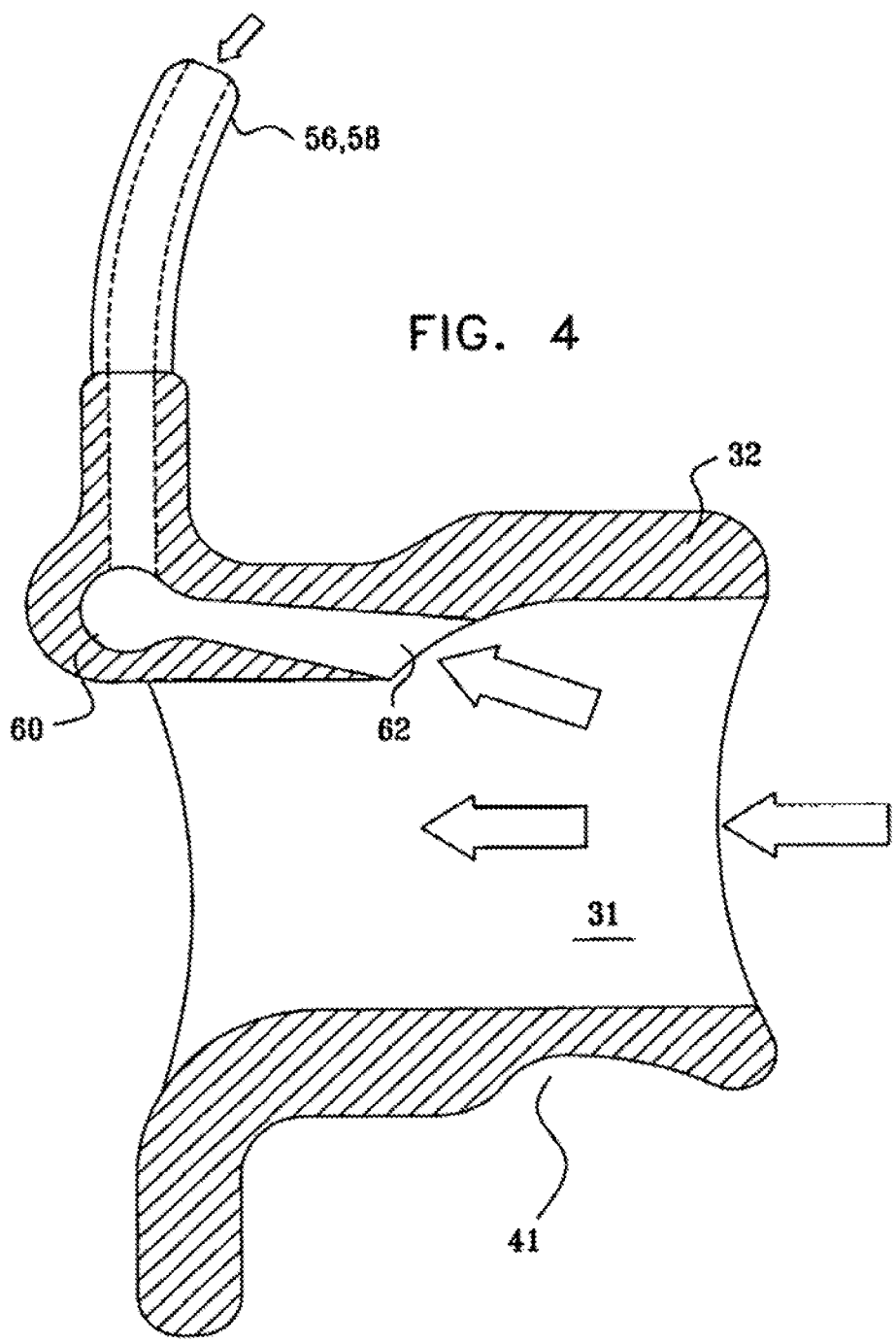
FIG. 4 is a cross-sectional drawing of the bite block of FIG. 3, to illustrate the way in which the oral breath monitoring is performed.

Reference is now made to FIG. 4, which is a cross-sectional drawing of the endoscopic bite block of FIG. 3, viewed along the plane marked AA in FIG. 3, to illustrate the way in which the oral breath monitoring is accomplished. The body of the capnographic bite block has an oral breath sampling channel 62 built into the roof of the central channel. Part of the exhaled oral breath flowing in the central channel 36 of the capnographic bite block flows into this sampling channel, and is collected by the collection tube 60 for transfer to the capnographic monitor, together with the nasal exhaled breath collected through the nasal prongs 56, 58. Flow of exhaled breath into the sampling channel is aided by the shape of the central roof, in which the entry port of the sampling channel is preferably positioned jutting out of the roof in a scoop configuration, such that it readily intercepts part of the exhaled breath flow.

Figure 5:
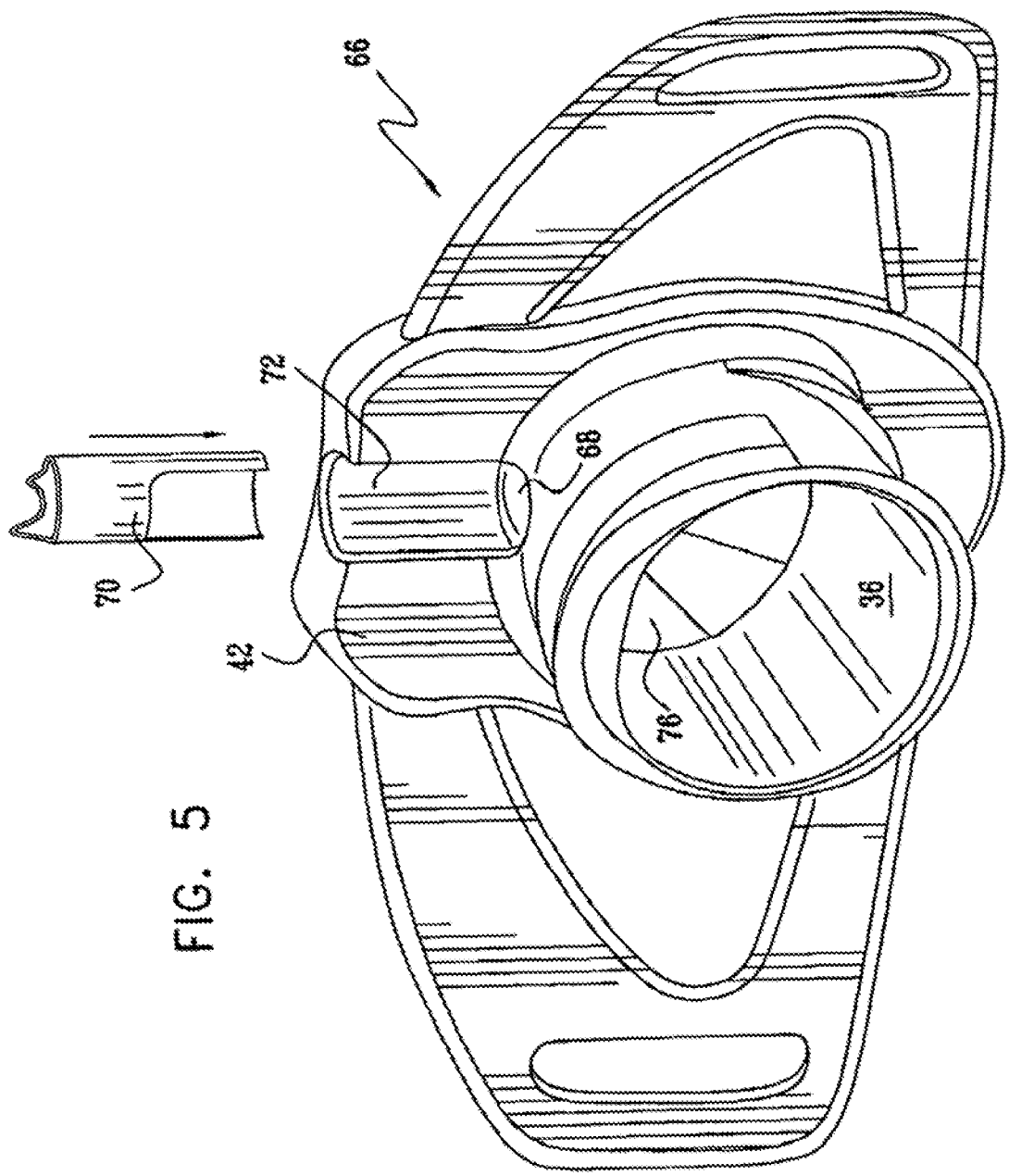
FIG. 5 is a schematic isometric view of another endoscopic bite block, constructed and operative according to a further preferred embodiment of the present invention, intended for use with a separate oral/nasal cannula.

Reference is now made to FIG. 5, which is a schematic isometric view from the rear of another capnographic bite block 66, constructed and operative according to a further preferred embodiment of the present invention. The bite block is intended for use with a separate oral/nasal cannula, such as that described, in the above-mentioned U.S. Pat. No. 6,422,240. An exemplary embodiment of the separate oral/nasal cannula is depicted in FIG. 8. The oral/nasal cannula has a pair of nasal prongs 56, 58 for insertion into the nostrils of a patient and an oral prong 70 for placement near the oral cavity of the patient (not shown) to form an oral/nasal cannula. The cannula also has a collection tube 60 for collection of the exhaled gases for analysis by a capnograph (not shown). Nasal prongs 56, 58, oral prong 70 and collection tube 60 meet at a single junction 84, preferably at exactly one junction. It is preferable to minimize the single junction 84 to reduce void volume.

The subject preferably puts on the cannula before the bite block is inserted into the subject's mouth, and it is operated as a standard sampling and delivery cannula. The bite block 66 has an opening 68 in the roof of the channel 36, extending into the channel, and the end of the oral sampling prong 70 of the cannula is arranged to terminate close to this opening, or even to just project into this opening such that its tip just projects into the top of the channel. In this position, the oral prong is able to sample the orally exhaled breath stream without being disturbed by, and without disturbing, the insertion of the endoscopic probe through the bite block. In order to increase the collection efficiency of the oral sampling prong, the point at which the opening breaks through into the central channel can preferably be provided with a small scoop, not visible in the drawing of FIG. 5, though shown below in FIG. 6, and directed inwards into the direction of the subject's mouth, such that it samples the breath stream more effectively. The wall of the tip of the oral prong 70 in the direction of the subject's mouth is preferably cut away, leaving the wall at the front of the prong end intact to intercept the oral breath flow more efficiently. Furthermore, since the bite block of the present invention enables use of the same cannula both before, during and after the bite block is in the subject's mouth, this cut-away tip is useful for ensuring efficient interception and sampling of the exhaled breath even without the bite block. Such a cut away tip has a further function, as will be described hereinbelow in relation to the details shown in FIG. 6.

According to a further preferred embodiment of the present invention, a groove or recess 72 is provided in the center of the top of the front plate of the bite block, in which the oral probe sits when the bite block is inserted in place in the subject's mouth. In practice, the bite black can be simply placed straight into the mouth of the subject, over the oral prong, and the front plate is operative to hold the oral prong snuggly within the recess, thus ensuring the stability of its desired sampling position within the opening. In this respect, the other above-described features of the bite block of the present invention, which contribute to the comfort and accuracy of the positioning of the bite block within the mouth and against the subject's lips, also ensure that the oral probe is held positively in its desired sampling position within the groove in the front plate. The groove is also operative to compensate for slight differences in the size of the facial features of the subject, since when the oral probe is tightly held in the groove between the groove and the subject's upper lip, even if the tip of the oral prong does not reach its optimal position near the bottom of the groove, the groove conducts the sampled breath from the sampling opening to the end of the oral prong.

The bite block of FIG. 5 has slightly different design features for the teeth positioning features to those shown in FIGS. 2A to 3, but the functional purpose and result is identical.

It is important that, in those embodiments where a scoop is not provided, the end of the cannula just reaches its predefined position close to the roof of the central channel of the bite block, without protruding into the central channel too much, and without falling short thereof too much. This condition should preferably be achieved independently of the different height of the upper lip dimension of different subjects. In order to ensure this, according to further preferred embodiments of the present invention, the oral prong of the cannula can preferably be provided with an adjustable sliding section enabling the effective length of the oral prong to be adjusted to suit the subject's facial features. This enables compensation to be made for the different position acquired by the end of the oral prong before and after inserting the bite block, when the position of the tip would change relative to the mouth because of the wide opening needed with the bite block inserted.

Alternatively and preferably, a cannula with a fixed oral prong could be used, and the opening in the roof of the bite block provided with a tubular chimney at its top end, into which the oral prong of the cannula is threaded. The length of the oral prong is selected such that the end of the oral prong is always situated within the chimney, regardless of differences in the size of the facial features of the subject. According to this embodiment, the oral prong should fit into the tubular chimney without an excessive gap, so that excessive leakage or dilution of the sampled gas is prevented. The use of the recessed groove embodiment though, may in many situations be more advantageous than the chimney embodiment, since the former more readily enables a cannula with a standard length oral prong to be used, such that the same cannula can be used by the subject both before, during and after the bite block has been used.

Figure 6:
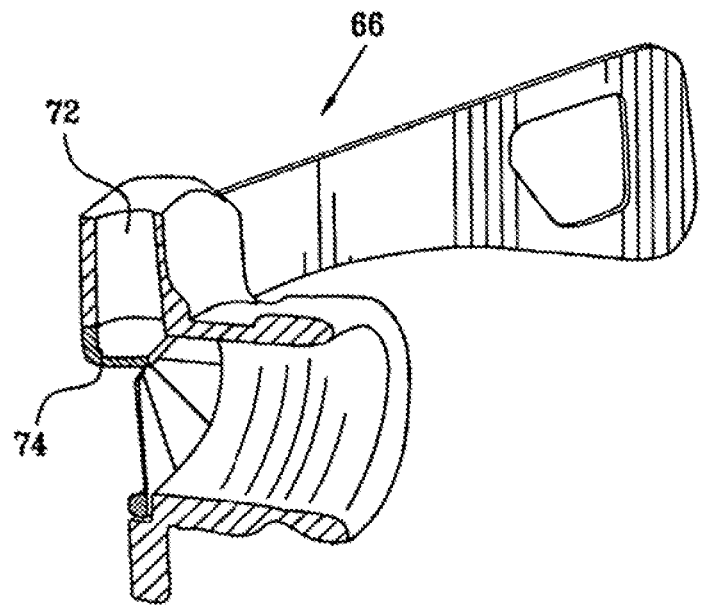
FIG. 6 is a schematic drawing of the bite block of FIG. 5, cut away down its center line to show a preferred embodiment of the oral breath directing scoop.

Reference is now made to FIG. 6, which is a schematic drawing of the bite block of FIG. 5, cut-away down its centerline to show a preferred embodiment of the oral breath directing scoop 74 at the bottom of the groove 72 the oral sampling prong of the cannula. The thin spoon shape of the scoop effectively becomes the roof of the central channel, separating between the endoscope probe and the oral prong. Using this embodiment, the base of the scoop prevents the oral prong from protruding into the channel too much and from being occluded or moved by the endoscope probe. The cut-away tip of the oral probe, as shown in FIG. 5, is also important to prevent the end of the oral probe from being blocked if the tip is inserted to the floor of the scoop.

At the front end of the bite block shown in FIG. 5, there is shown an additional feature 76, according to a further preferred embodiment of the bite block of the present invention, which attempts to solve the problem of efficient capnographic sampling in the situation when open mouth breathing is the main form of breathing being done by the subject. The cross sectional area of the bite block inner channel 36 is generally closed off near its outer end, forward of the plane of the oral sampling probe opening 68, by means of a flexible curtain 76, composed of flaps, so as to generate an inner volume in the inside of the bite block, substantially isolated from the external air, except for a small hole through which the subject inhales and exhales and at which the inhaled and exhaled breath stream can sampled. The flexible curtain flaps are preferably made of a thin plastic material, selected to be of the correct thickness that they maintain their position when undisturbed, yet bend readily when pushed by the endoscope probe, thus not limiting the endoscope maneuvers. The plastic material is also preferably transparent so that the physician can see inside the oral cavity while he is inserting and maneuvering the endoscope probe.

Figure 7:
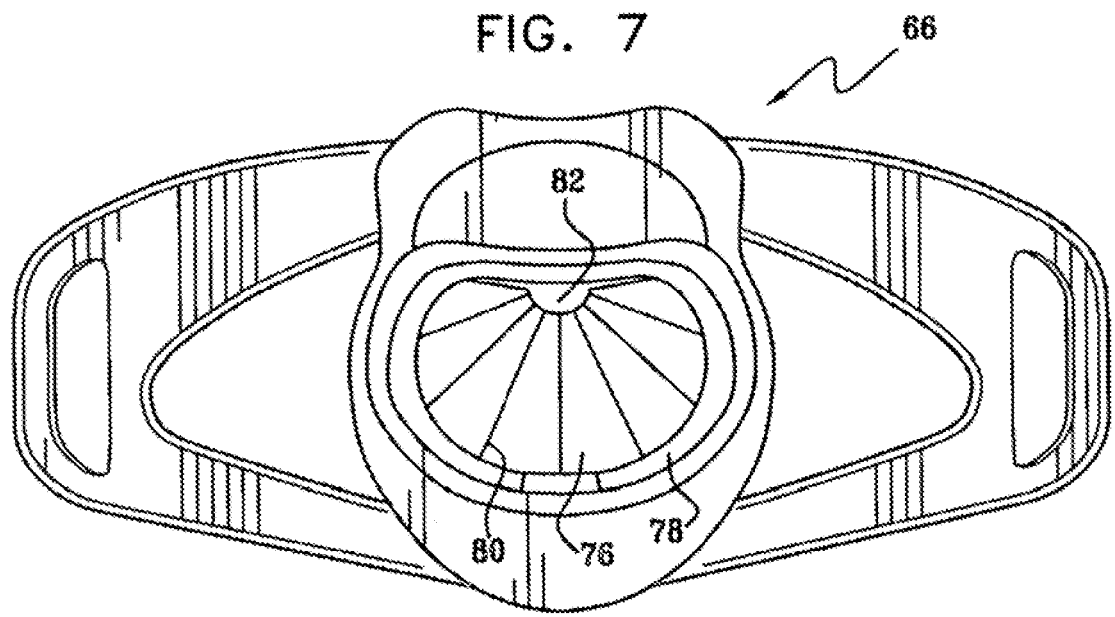
FIG. 7 is a view from the front of the bite block of FIG. 5, to illustrate a preferred shape of a closure curtain at its front end, according to a further preferred embodiment of the present invention.

Reference is now made to FIG. 7, which is a view from the front of the bite block 66 of FIG. 5, to illustrate a preferred shape of the plastic curtain 76 and its flaps. The curtain is preferably attached to the front plate of the bite block around its periphery 78, and the flaps are preferably formed by means of slits 80 across the surface of the curtain, from the periphery towards a point within its cross section, so that the flaps open without hindrance when an endoscopic probe is inserted into the bite block. However, the flaps pushed aside by the endoscopic probe close back around the probe once it has been inserted, and thus still maintain a largely closed oral cavity volume, from which capnographic sampling can be performed accurately. In the preferred embodiment shown in FIG. 7, the vertex of the flap structure is shown near the top of the cross section of the bite block channel, but it is to be understood that the slits can be provided in any form which allows easy bending and effective sealing once the endoscopic probe has been inserted into the bite block. A small hole 82 is also preferably provided in the slit curtain to enable easy expulsion and inhalation of the subject's breaths. This hole is preferably placed close to the sampling opening in the roof of the central channel, so that the flow passing the opening has good inhalation and exhalation exchange attributes. Under these conditions, the samples collected for the capnographic analysis are authentic samples of the exhaled and inhaled breath of the subject. Additionally, because of the isolated volume within the bite block, which is operative to direct and concentrate the breath sample, both pressure and flow wise towards the breathing hole, which is the only substantial exit, and to isolate it from the outside, the sample is substantially undiluted by extraneous air during exhalation. The accuracy of the capnographic measurement is therefore good.

The various features of the bite block of the present invention include, inter alia, teeth positioning features, front plate alignment, attaching band positions, openings for using the oral prong of separate oral/nasal cannulae, blocking curtain flaps for closing off the internal volume of the bite block, and others. It is to be understood that this invention is not meant to be limited to the specific combinations of features described in the preferred embodiments described above in this application, but rather that any combination of the various features of the preferred embodiments described can be used in one endoscopic bite block, or any feature can even be used separately in a bite block, thereby providing the individual advantages of that feature to the bite block.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An endoscopic bite block, comprising:
    a central channel comprising an upper wall having an upper outer surface, and a lower wall having a lower outer surface;
    a breath sampling channel configured to sample orally exhaled breath;
    a front plate merged with an outer end section of said central channel, said front plate comprising an upper and a lower section;
    a groove formed within a wall of said upper section, such that said wall of said upper section circumferentially delimits said groove; wherein said groove receives a nasal prong when in use; and
    a collection tube connectable to said breath sampling channel, said collection tube configured to receive the orally exhaled breath sampled by said breath sampling channel.

2. The endoscopic bite block according to claim 1, wherein said front plate further comprises connecting points for attaching said bite block to a subject, said connecting points located above a horizontal center line of said bite block.

3. The endoscopic bite block according to claim 1, wherein the nasal prong is one of a gas collecting cannula and a gas delivery cannula.

4. The endoscopic bite block according to claim 3, wherein said gas collecting cannula further comprises an oral collection channel.

5. The endoscopic bite block according to claim 3, wherein said gas delivery cannula comprises at least one of nasal and oral outlets.

6. The endoscopic bite block according to claim 1, further comprising a penetrable curtain disposed in said outer end section of said central channel across a majority of an internal cross section of said central channel thereby substantially preventing flow of gases across said majority of said cross section.

7. The endoscopic bite block according to claim 1, further comprising teeth positioning regions across at least part of said upper outer surface of said upper wall and across at least part of said lower outer surface of said lower wall of said central channel, said teeth positioning region in said upper wall being disposed outwardly relative to said teeth positioning region in said lower wall.

8. The endoscopic bite block according to claim 7, wherein at least one of said upper and lower outer surfaces has a generally flattened portion on which its associated teeth positioning region is disposed.

9. The endoscopic bite block according to claim 7, wherein at least one of said teeth positioning regions is curved in a plane of its associated surface to approximate the curve of the teeth in a human jaw.

10. The endoscopic bite block according to claim 7, wherein at least one of said teeth positioning regions is a lowered platform region in its associated surface.

11. The endoscopic bite block according to claim 1, wherein said collection tube is further configured to receive nasal exhaled breath from nasal prongs received within said groove.

12. The endoscopic bite block according to claim 1, wherein said upper and lower outer surfaces comprise a material softer than that of the front plate of the bite block at an outer end section thereof.

* * * * *